United States Patent
Suzuki et al.

(10) Patent No.: US 11,612,912 B2
(45) Date of Patent: Mar. 28, 2023

(54) ULTRASOUND TRANSDUCER AND ULTRASOUND DIAGNOSTIC APPARATUS

(71) Applicant: KONICA MINOLTA, INC., Tokyo (JP)

(72) Inventors: Kenji Suzuki, Tokyo (JP); Yuta Nakayama, Chiba (JP)

(73) Assignee: KONICA MINOLTA, INC., Tokyo (JP)

( * ) Notice: Subject to any disclaimer, the term of this patent is extended or adjusted under 35 U.S.C. 154(b) by 579 days.

(21) Appl. No.: 16/161,544

(22) Filed: Oct. 16, 2018

(65) Prior Publication Data

US 2019/0118223 A1    Apr. 25, 2019

(30) Foreign Application Priority Data

Oct. 19, 2017 (JP) .............................. JP2017-202923

(51) Int. Cl.
| | |
|---|---|
| *B06B 1/06* | (2006.01) |
| *A61B 8/00* | (2006.01) |
| *H01L 41/257* | (2013.01) |
| *H01L 41/09* | (2006.01) |
| *B06B 1/02* | (2006.01) |

(52) U.S. Cl.
CPC .......... *B06B 1/0629* (2013.01); *A61B 8/4494* (2013.01); *A61B 8/54* (2013.01); *B06B 1/0207* (2013.01); *H01L 41/0973* (2013.01); *H01L 41/257* (2013.01); *B06B 1/0215* (2013.01)

(58) Field of Classification Search
CPC ....... A61B 8/54; A61B 8/4494; H01L 41/257; H01L 41/0973; B06B 1/0207; B06B 1/0215; B06B 1/0629

USPC ........................................................ 310/311
See application file for complete search history.

(56) References Cited

U.S. PATENT DOCUMENTS

| | | |
|---|---|---|
| 5,163,436 A | 11/1992 | Saito et al. |
| 5,619,476 A | 4/1997 | Haller et al. |
| 5,870,351 A | 2/1999 | Ladabaum et al. |
| 6,004,832 A | 12/1999 | Haller et al. |
| 9,061,320 B2 | 6/2015 | Hajati et al. |
| 9,345,450 B2 | 5/2016 | Corl |
| 9,475,093 B2 | 10/2016 | Hajati et al. |
| 10,231,708 B2 | 3/2019 | Suzuki |
| 2009/0001853 A1* | 1/2009 | Adachi ................. B06B 1/0292 310/323.19 |

(Continued)

FOREIGN PATENT DOCUMENTS

| | | |
|---|---|---|
| JP | H04211600 A | 8/1992 |
| JP | 2015517752 A | 6/2015 |

(Continued)

OTHER PUBLICATIONS

Japanese Office Action (and English language translation thereof) dated Apr. 27, 2021 issued in Japanese Application No. 2017-202923.

*Primary Examiner* — Shawki S Ismail
*Assistant Examiner* — Monica Mata
(74) *Attorney, Agent, or Firm* — Holtz, Holtz & Volek PC

(57) ABSTRACT

An ultrasound transducer in which a plurality of pMUT cells are arranged. The pMUT cells have a plurality of resonance frequencies. Each of the pMUT cells includes a piezoelectric film that is polarized in a first direction that is a thickness direction or a second direction that is opposite to the first direction.

8 Claims, 8 Drawing Sheets

(56) References Cited

U.S. PATENT DOCUMENTS

| | | | |
|---|---|---|---|
| 2014/0117812 A1* | 5/2014 | Hajati | H01L 41/331 310/314 |
| 2014/0180128 A1 | 6/2014 | Corl | |
| 2015/0054387 A1* | 2/2015 | Li | H01L 41/0805 310/363 |
| 2016/0228094 A1 | 8/2016 | Corl | |
| 2019/0290242 A1* | 9/2019 | Suzuki | B06B 1/064 |
| 2020/0143791 A1* | 5/2020 | Halbach | G06F 3/016 |

FOREIGN PATENT DOCUMENTS

| | | |
|---|---|---|
| JP | 2016030019 A | 3/2016 |
| JP | 2016507270 A | 3/2016 |
| JP | 2016541136 A | 12/2016 |

\* cited by examiner

ULTRASOUND TRANSDUCER AND ULTRASOUND DIAGNOSTIC APPARATUS

CROSS REFERENCE TO RELATED APPLICATIONS

The entire disclosure of Japanese Patent Application No. 2017-202923 filed on Oct. 19, 2017, is incorporated herein by reference in its entirety.

BACKGROUND

Technological Field

The present invention relates to an ultrasound transducer and an ultrasound diagnostic apparatus.

Description of Related Art

In recent years, a piezoelectric micromachined ultrasound transducer (pMUT) and a capacitive micromachined ultrasonic transducer (cMUT) have been developed by using a semiconductor microfabrication technique (micro electro mechanical system: MEMS) as an ultrasound transducer (which may be referred to as an ultrasound probe or an ultrasonic probe) of an ultrasound diagnostic apparatus. A piezoelectric cell (vibrator) of an ultrasound transducer using the MEMS, which is excellent in high-frequency suitability and high sensitivity, has a problem of a narrowband characteristic. To solve the above problem, the description of U.S. Pat. No. 5,870,351 discloses a technique of achieving a wider band by allowing a cell having a vibrating membrane of a high spring constant and a cell having a vibrating membrane of a low spring constant to coexist in a capacitive micromachined ultrasonic transducer (cMUT). Japanese Unexamined Patent Application Publication (Translation of PCT Application) No. 2015-517752 discloses a technique that not only achieves a wider band by allowing pMUTs having resonance frequencies different from each other to coexist, but also reduces crosstalk by shifting resonance frequencies of adjacent channel cells from each other.

As described above, a technique of adjusting an amplitude characteristic relating to a resonance frequency of each piezoelectric cell has been developed. However, a piezoelectric cell has a phase characteristic in addition to an amplitude characteristic. When a plurality of piezoelectric cells having different phase characteristics are driven at the same time, sound pressures of the piezoelectric cells cancel each other (are antibonded) when a phase is inverted. As a result, an entire output sound pressure is lowered and a narrow band is formed, causing an ultrasound transducer to have lowered sensitivity. For this reason, there has been demand for an ultrasound transducer that can obtain a wide-band characteristic by matching phases of piezoelectric cells.

SUMMARY

An object of the present invention is to provide an ultrasound transducer and an ultrasound diagnostic apparatus including a plurality of piezoelectric cells having different resonance frequencies that can obtain a wide-band characteristic by matching phases of the piezoelectric cells.

In order to realize at least one of the above objects, an ultrasound transducer reflecting an aspect of the present invention is an ultrasound transducer in which a plurality of pMUT cells are arranged, in which the plurality of pMUT cells have one of a plurality of resonance frequencies, and each of the plurality of pMUT cells includes a piezoelectric film that is polarized in a first direction that is a thickness direction or a second direction that is opposite to the first direction.

An ultrasound diagnostic apparatus reflecting an aspect of the present invention includes the above ultrasound transducer.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

In the following, like numerals denote components having like function and configuration, and the description thereof will be omitted.

First Embodiment

Hereinafter, a first embodiment of the present invention will be described.

[Configuration of Ultrasound Diagnostic Apparatus]

Figure 1:
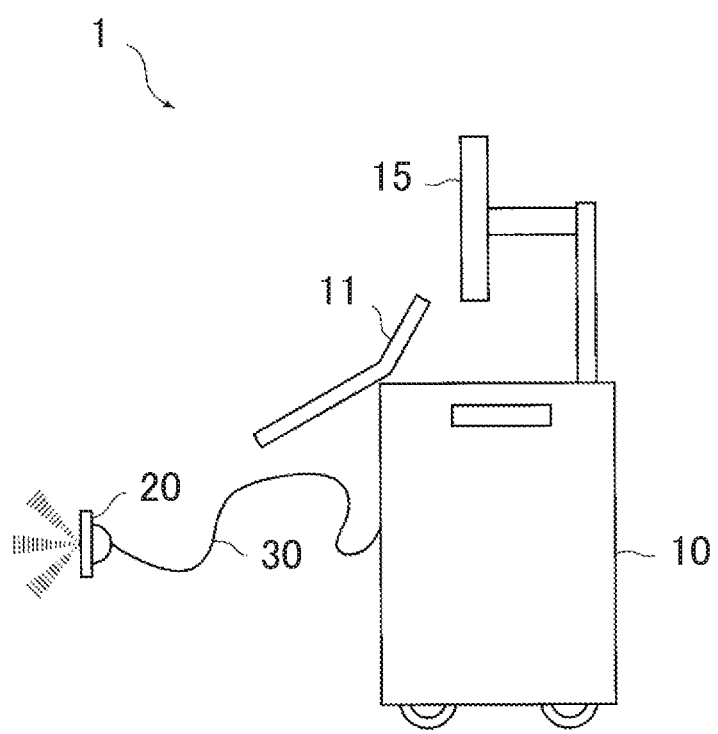
FIG. 1 is a diagram showing an appearance configuration of an ultrasound diagnostic apparatus.
Figure 2:
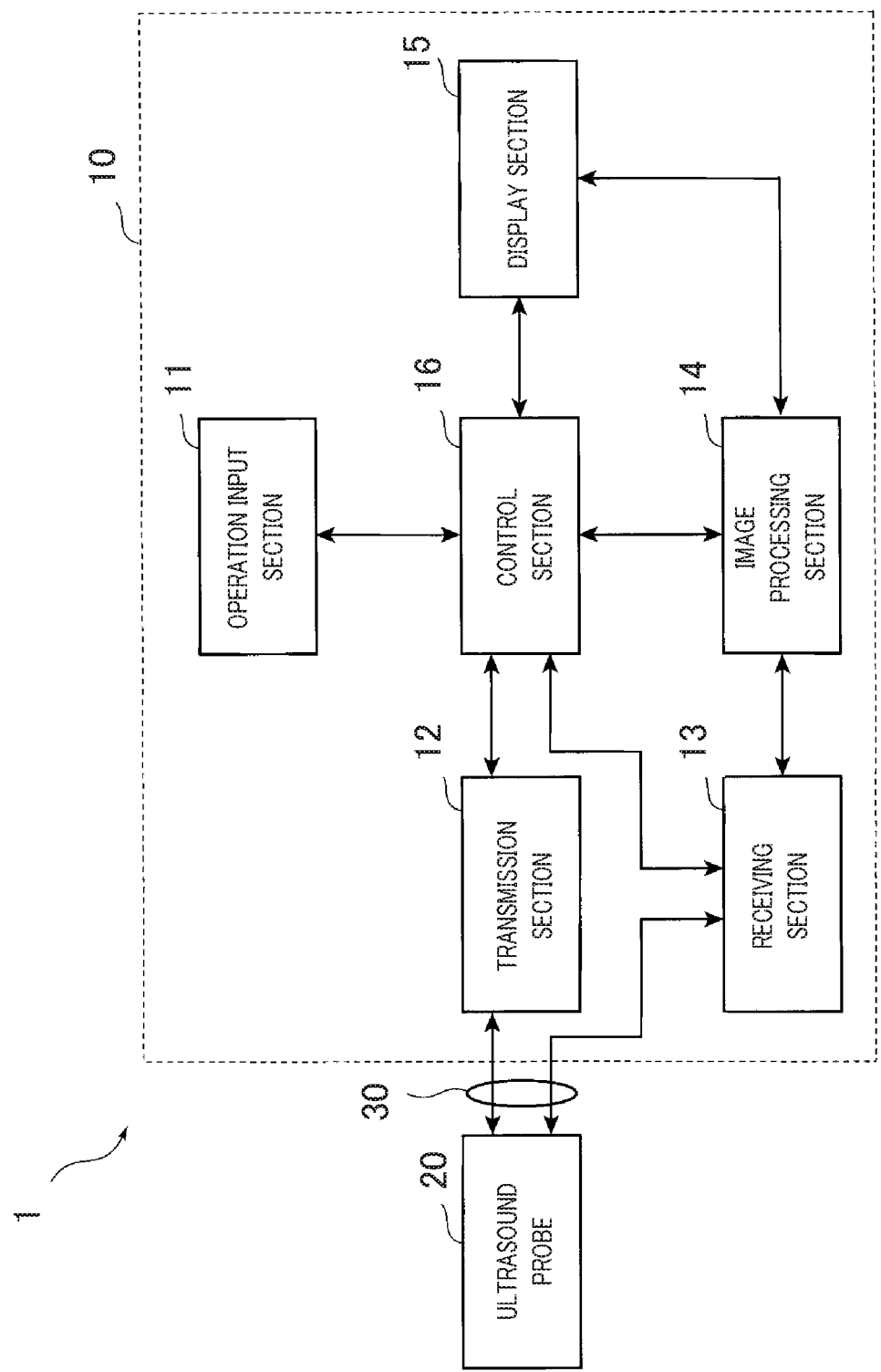
FIG. 2 is a block diagram showing an electric configuration example of the ultrasound diagnostic apparatus.

FIG. 1 is a diagram showing an appearance configuration of an ultrasound diagnostic apparatus according to the present embodiment. FIG. 2 is a block diagram showing an electric configuration example of the ultrasound diagnostic apparatus according to the present embodiment.

An ultrasound diagnostic apparatus 1 employs a configuration that includes ultrasound diagnostic apparatus main body 10, ultrasound probe 20, and cable 30.

Ultrasound probe 20 transmits an ultrasound signal to a human body (not shown) as a test object, and receives an ultrasound signal reflected by the human body.

The ultrasound diagnostic apparatus main body 10, which is connected to ultrasound probe 20 via cable 30, transmits an electrical transmission signal to ultrasound probe 20 via cable 30 to cause ultrasound probe 20 to transmit an ultrasound signal. Ultrasound diagnostic apparatus main body 10 also obtains an ultrasound image of an internal state of a human body by using an electrical signal generated by ultrasound probe 20 based on an ultrasound signal received by ultrasound probe 20.

Specifically, ultrasound diagnostic apparatus main body 10 employs a configuration that includes operation input section 11, transmission section 12, receiving section 13, image processing section 14, display section 15, and control section 16.

Operation input section 11 inputs, for example, a command for instructing start of diagnosis and the like or information relating to a test object. Operation input section 11 is, for example, an operation panel including a plurality of input switches, or a keyboard.

Transmission section 12 transmits a control signal (drive signal) received from control section 16 to ultrasound probe 20 via cable 30.

Receiving section 13 receives a signal transmitted from ultrasound probe 20 via cable 30. Receiving section 13 then outputs the received ultrasound signal to image processing section 14.

Image processing section 14 generates an image (ultrasound image) used for ultrasound diagnosis that shows the internal state of a test object by using the ultrasound signal received from receiving section 13 in accordance with an instruction from control section 16.

Display section 15 displays the ultrasound image generated by image processing section 14 in accordance with an instruction from control section 16.

Control section 16 controls operation input section 11, transmission section 12, receiving section 13, image processing section 14, and display section 15 in accordance with their functions to control entire ultrasound diagnostic apparatus 1. Control section 16 also controls ultrasound probe 20 via transmission section 12 and receiving section 13.

[Configuration of Ultrasound Probe 20]

Figure 3:
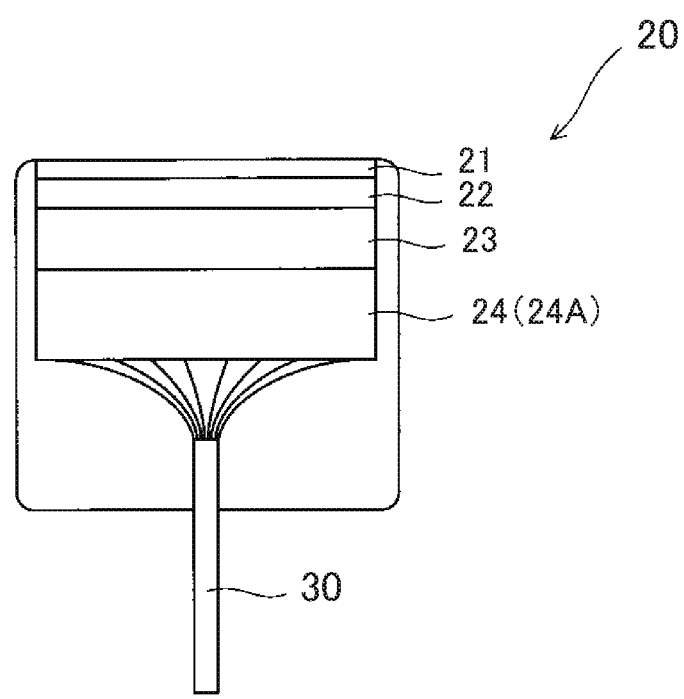
FIG. 3 is a diagram for explaining a configuration of an ultrasound probe.

FIG. 3 is a diagram for explaining a configuration of ultrasound probe 20. Ultrasound probe 20 includes protection layer 21, pMUT element 22, backing material 23, and signal processing circuit 24 (signal processing circuit 24A in a second embodiment described later).

Protection layer 21 protects pMUT element 22. Protection layer 21 is formed of comparatively soft silicone rubber or the like that does not cause an uncomfortable feeling when being in contact with a human body, and has an acoustic impedance close to that of a human body.

pMUT element 22 is a pMUT array on which a plurality of pMUT cells, that are manufactured by using the micro electro mechanical systems (MEMS) technology, are arranged. The plurality of pMUT cells constituting the pMUT element has one resonance frequency among a plurality of resonance frequencies (which will be described in detail later). An electrode wire is pulled out from each individual pMUT cell, and connected to signal processing circuit 24 described later.

Backing material 23 attenuates unnecessary vibration generated on pMUT element 22. Signal processing circuit 24 is a circuit that generates a pulse signal for ultrasound transmission, or performs processing of a received pulse signal, and the like, and is connected to ultrasound diagnostic apparatus main body 10 via cable 30.

Signal processing circuit 24 generates a drive signal for driving pMUT element 22 to transmit an ultrasound wave based on control of ultrasound diagnostic apparatus main body 10. Signal processing circuit 24 also applies predetermined signal processing to a received signal generated based on an ultrasound wave received by pMUT element 22 before transmitting the signal to ultrasound diagnostic apparatus main body 10.

[Configuration of Signal Processing Circuit 24]

Figure 4:
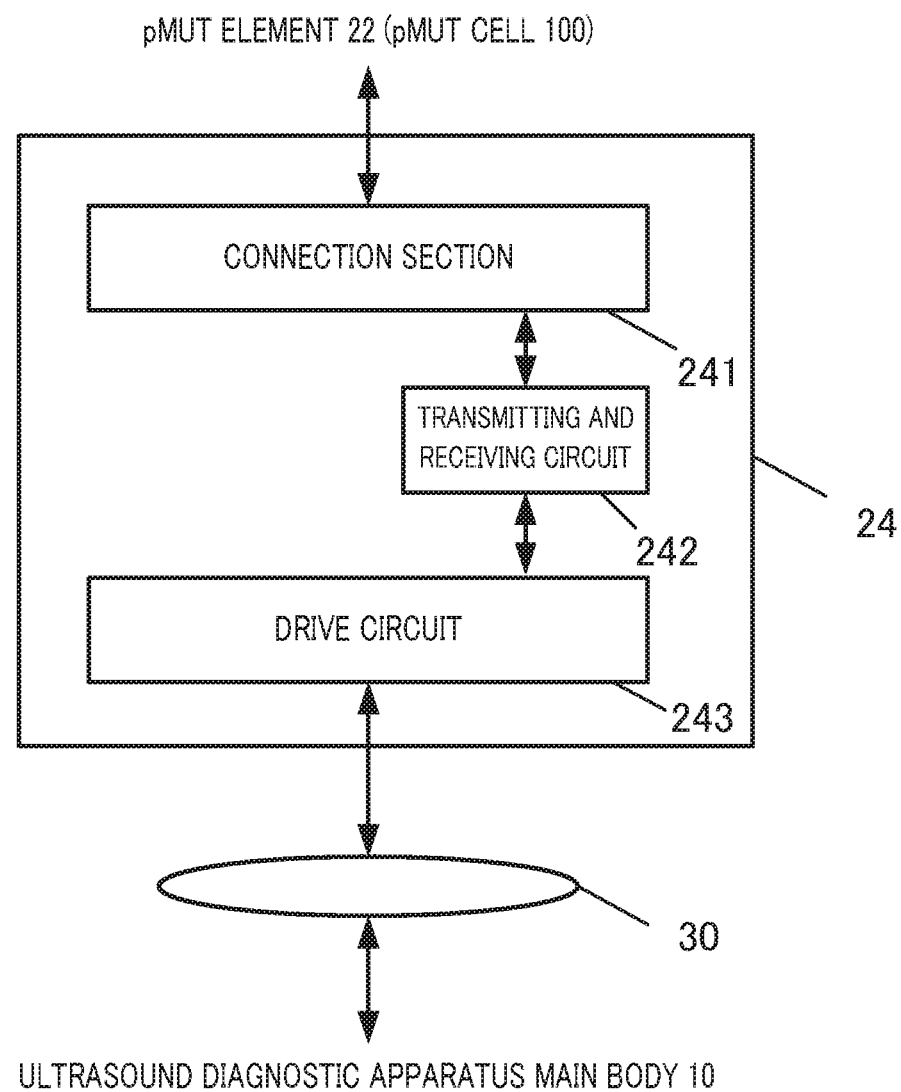
FIG. 4 is a block diagram showing a configuration example of a signal processing circuit of a first embodiment.

FIG. 4 is a block diagram showing a configuration example of signal processing circuit 24 of the first embodiment. As shown in FIG. 4, signal processing circuit 24 includes connecting section 241, transmitting and receiving circuit 242, and drive circuit 243. Connecting section 241 connects transmitting and receiving circuit 242 and an electrode wire pulled out from each pMUT cell 100 (refer to FIG. 5) of pMUT element 22.

Transmitting and receiving circuit 242 applies transmission control for transmitting an ultrasound wave via connecting section 241 to pMUT element 22 based on control of drive circuit 243. Transmitting and receiving circuit 242 also performs receiving control for transmitting a received signal generated based on an ultrasound wave received by pMUT element 22 to ultrasound diagnostic apparatus main body 10 via drive circuit 243.

Drive circuit 243 controls transmitting and receiving circuit 242 based on a control signal from ultrasound diagnostic apparatus main body 10. Drive circuit 243 also switches between transmission control and receiving control of transmitting and receiving circuit 242 as appropriate based on control of ultrasound diagnostic apparatus main body 10.

[Configuration of pMUT Element 22]

Figure 5:
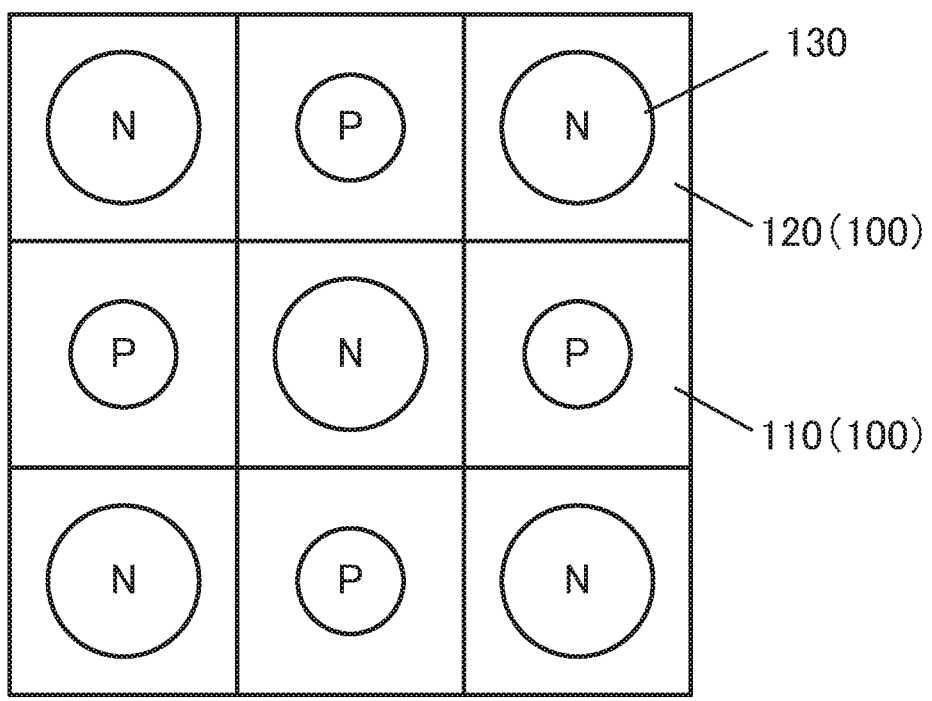
FIG. 5 is a diagram for explaining arrangement of pMUT cells on a pMUT element.

FIG. 5 is a diagram for explaining arrangement of pMUT cells 100 on pMUT element 22.

FIG. 5 exemplifies pMUT cells 100 that are arranged three-by-three two-dimensionally. The pMUT cell arrangement shown in FIG. 5 is part of pMUT element 22. In actuality, pMUT element 22 is constituted by arrangement of a larger number of pMUT cells 100. As shown in FIG. 5, in the present embodiment, high-frequency cells 110 and low-frequency cells 120 are arranged alternately in vertical and horizontal directions. In the present embodiment, high-frequency cell 110 has a comparatively high resonance frequency with piezoelectric film 130 that constitutes the cell and has a comparatively smaller diameter, and low-frequency cell 120 has a comparatively low resonance frequency with piezoelectric film 130 that constitutes the cell and has a comparatively large diameter.

Piezoelectric film 130 of each of pMUT cells 100 is polarized in a predetermined direction in advance. In the present embodiment, polarization directions of piezoelectric films 130 are opposite to each other between high-frequency cell 110 and low-frequency cell 120. That is, the polarization direction is inverted from low-frequency cell 120 side to high-frequency cell 110 side.

Piezoelectric film 130 is normally polarized in a thickness direction. When high-frequency cell 110 is polarized in a first direction (for example, a direction from a lower side of piezoelectric film 130 to an upper side), low-frequency cell 120 is polarized in a second direction (a direction from the upper side of piezoelectric film 130 to the lower side) that is opposite to the first direction. In the description hereinafter, the first direction will be described as polarization direction "P" and the second direction will be described as polarization direction "N".

A polarization direction of piezoelectric film 130 of each of pMUT cells 100 is preferably determined by, for example, polarization processing performed in a manufacturing process of pMUT element 22. In the polarization processing in a manufacturing process of pMUT element 22, each of pMUT cells 100 is polarized in polarization direction P or N by, for example, applying a predetermined voltage between an upper electrode and a lower electrode arranged to sandwich piezoelectric film 130.

Advantageous Effect of First Embodiment

As described above, in the first embodiment, pMUT element 22 has high-frequency cells 110 and low-frequency cells 120 arranged alternately in vertical and horizontal directions, and polarization directions of piezoelectric films 130 are opposite to each other between high-frequency cell 110 and low-frequency cell 120. By the above configuration, phases are matched between two adjacent ones of pMUT cells 100, and a situation where a frequency band, in which sensitivity is lowered due to phase mismatching, is generated can be avoided.

Conventionally, there have been methods of adjusting a viscosity coefficient by differentiating structures of pMUT cells depending on a resonance frequency as a method of matching phases of pMUT cells of a pMUT element. The above methods include a method of providing a hole on a support structure of a diaphragm constituted by a piezoelectric film, a method of sealing an opening section provided on a back surface of a diaphragm with resin or the like as appropriate, and a method of covering a diaphragm structure with resin or the like. However, when phases are matched by a method such as those described above, a structure needs to be changed for each cell, and manufacturing cost is increased.

There has also conventionally been a method of differentiating a transmission waveform between each pMUT cell as a method of matching phases of pMUT cells of a pMUT element. However, this method requires different transmission control for each of pMUT cells having different frequency characteristics, which leads to a complicated drive circuit and an increase in manufacturing cost.

In the first embodiment, the structure of pMUT element 22 is similar to a conventional one as described above, and phases can be controlled by polarization processing for each of pMUT cells 100 performed in a manufacturing process. Accordingly, phase matching can be preferably performed at low cost as compared with a conventional method.

Second Embodiment

Hereinafter, a second embodiment of the present invention will be described. In the first embodiment, a polarization direction is determined for each of pMUT cells 100 at the time of manufacture of pMUT element 22. The second embodiment is different from the first embodiment with respect to the point that a polarization direction of each of pMUT cells 100 can be controlled optionally. In the description of the second embodiment, configurations similar to those of the first embodiment will be attached with the same reference signs, and duplicate description will be omitted.

[Connection System of pMUT Cells 100]

First, a connection system of pMUT cells 100 will be described.

Figure 6A:
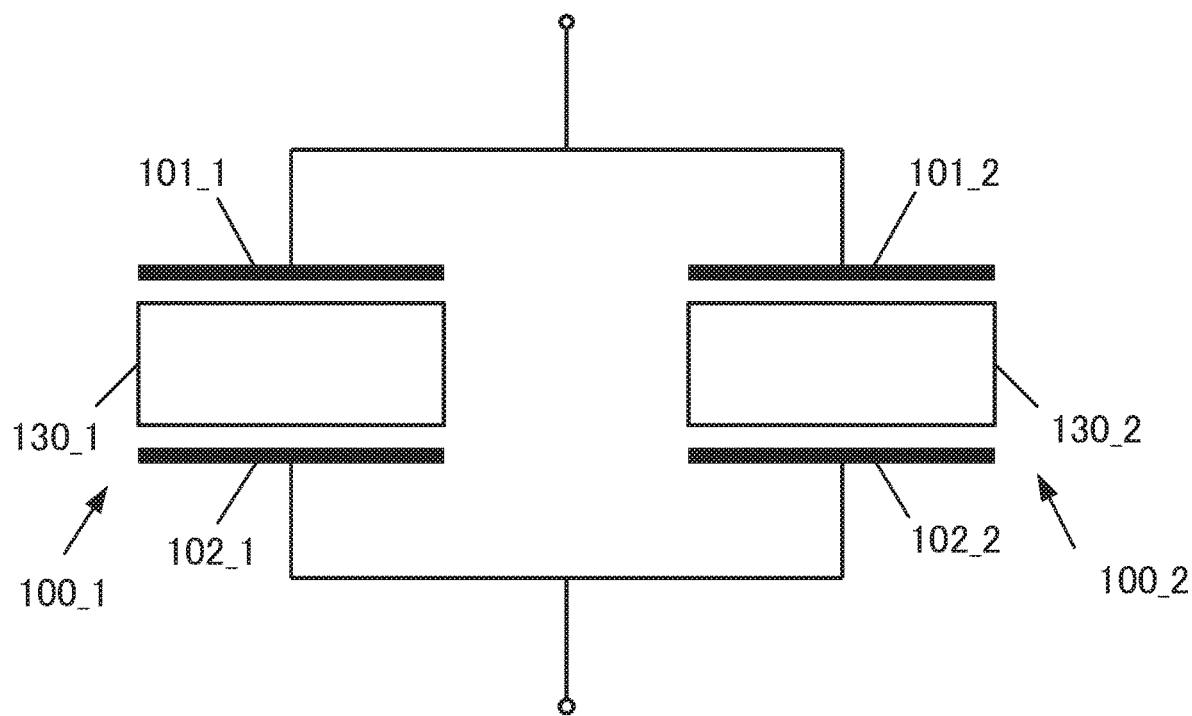
FIG. 6A is a diagram showing a configuration in which adjacent pMUT cells are connected in parallel.
Figure 6B:
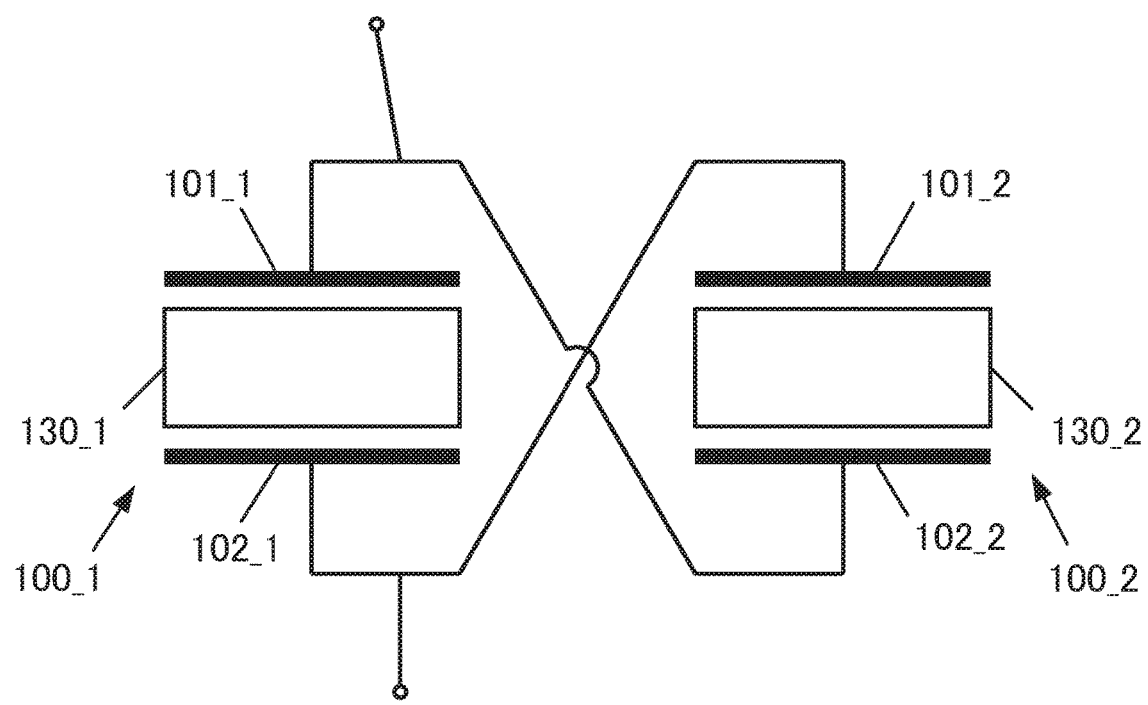
FIG. 6B is a diagram showing a configuration in which adjacent pMUT cells are connected in series.

FIGS. 6A and 6B are diagrams for explaining a connection system of adjacent ones of pMUT cells 100. FIG. 6A shows a configuration in which pMUT cells 100_1 and 100_2 adjacent to each other are connected in parallel. FIG. 6B shows a configuration in which pMUT cells 100_1 and 100_2 adjacent to each other are connected in series. Although omitted from illustration, pMUT cells 100_1 and 100_2 are connected to other pMUT cells (not shown) in a similar manner.

When pMUT cells 100_1 and 100_2 are connected in parallel as shown in FIG. 6A, upper electrode 101_1 of pMUT cell 100_1 and upper electrode 101_2 of pMUT cell 100_2 are connected, and lower electrode 102_1 of pMUT cell 100_1 and lower electrode 102_2 of pMUT cell 100_2 are connected. Piezoelectric film 130_1 of pMUT cell 100_1 is provided below and above upper electrode 101_1 and lower electrode 102_1, and piezoelectric film 130_2 of pMUT cell 100_2 is provided below and above upper electrode 101_2 and lower electrode 102_2.

On the other hand, when pMUT cells 100_1 and 100_2 are connected in series as shown in FIG. 6B, upper electrode 101_1 of pMUT cell 100_1 and lower electrode 102_2 of pMUT cell 100_2 are connected, and lower electrode 102_1 of pMUT cell 100_1 and upper electrode 101_2 of pMUT cell 100_2 are connected.

[Configuration of Signal Processing Circuit 24A]

Figure 7:
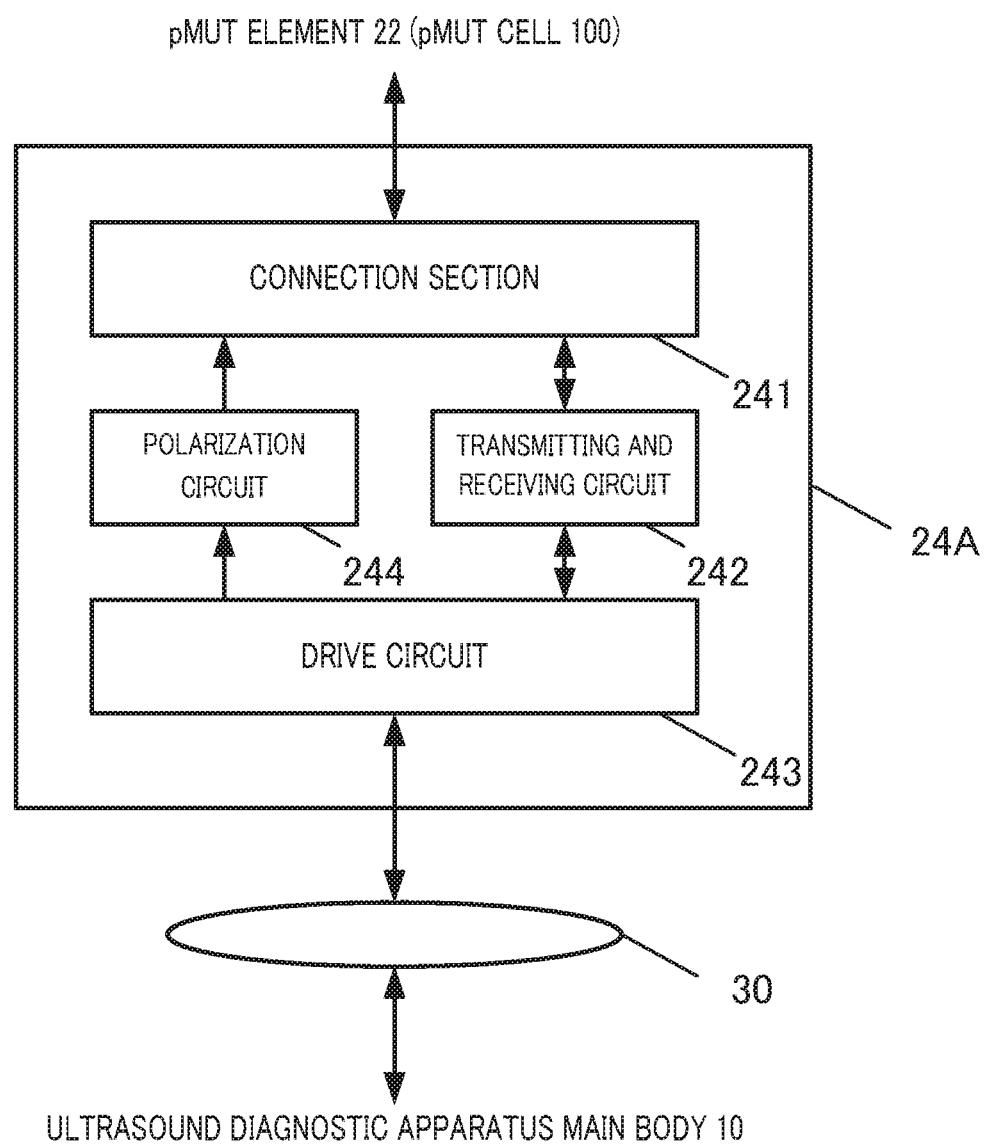
FIG. 7 is a block diagram showing a configuration example of the signal processing circuit of a second embodiment.

Next, signal processing circuit 24A in the second embodiment will be described. FIG. 7 is a block diagram showing a configuration example of signal processing circuit 24A. As shown in FIG. 7, signal processing circuit 24A in the second embodiment includes polarization circuit 244 in addition to the configuration of signal processing circuit 24 in the first embodiment. Polarization circuit 244 is an example of the polarization section of the present invention.

Connecting section 241 connects transmitting and receiving circuit 242 and polarization circuit 244 and an electrode wire pulled out from each of pMUT cells 100 of pMUT element 22 in the second embodiment.

Transmitting and receiving circuit 242 applies transmission control for transmitting an ultrasound wave via connecting section 241 to pMUT element 22 based on control of drive circuit 243. Transmitting and receiving circuit 242 also performs receiving control for transmitting a received signal generated based on an ultrasound wave received by pMUT element 22 to ultrasound diagnostic apparatus main body 10 via drive circuit 243.

Drive circuit 243 controls transmitting and receiving circuit 242 and polarization circuit 244 based on a control signal from ultrasound diagnostic apparatus main body 10. Drive circuit 243 that controls polarization circuit 244 is an example of the controller of the present invention.

Polarization circuit 244 performs polarization processing by applying a predetermined voltage to piezoelectric film 130 of each of pMUT cells 100 of pMUT element 22 under the control of drive circuit 243. By the polarization processing, two adjacent ones of pMUT cells 100 are inversely polarized, so that phases of adjacent ones of pMUT cells 100 are matched.

[Configuration of Polarization Circuit 244]

Figure 8:
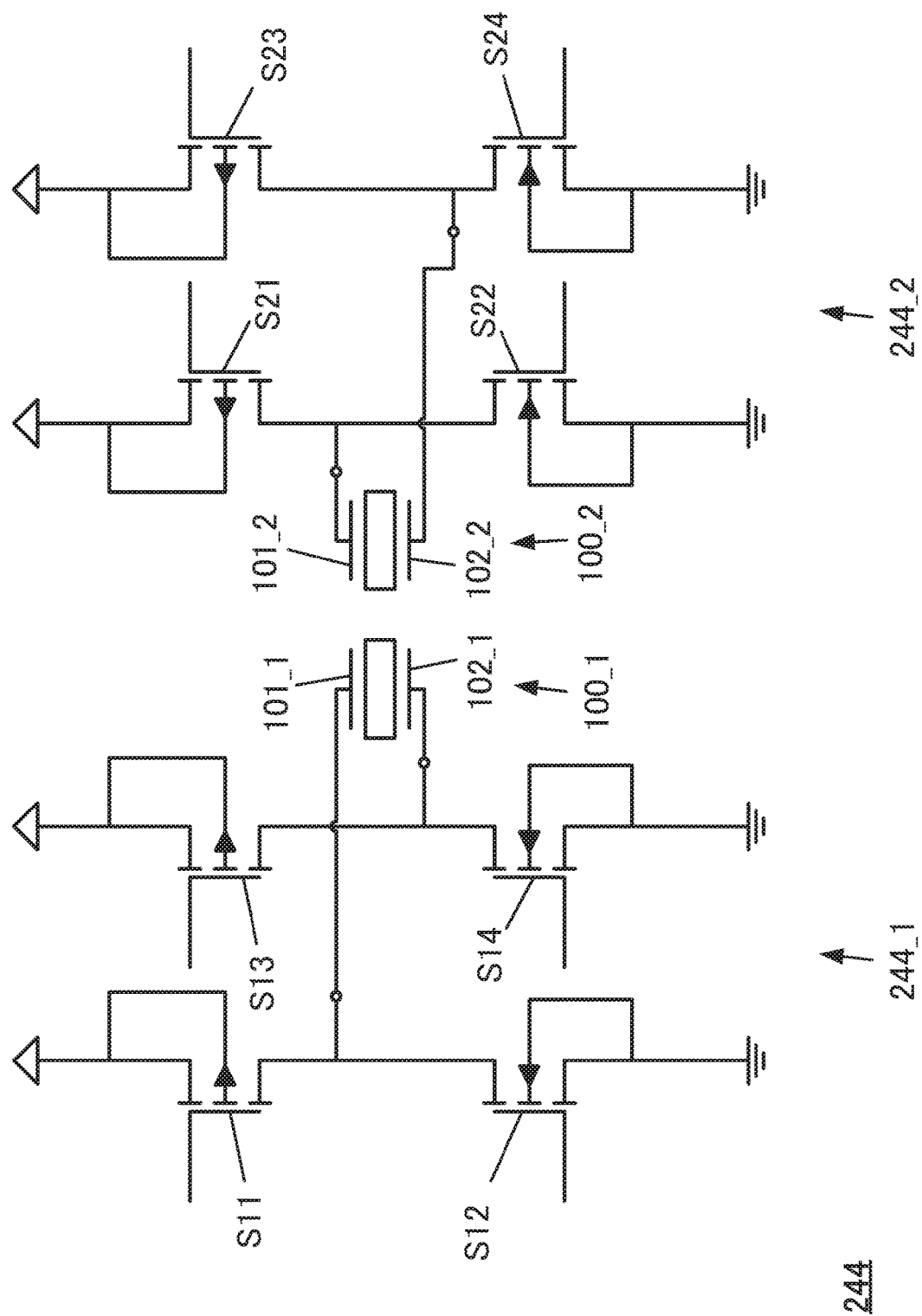
FIG. 8 is a diagram for explaining a cell polarization circuit constituting a polarization circuit.

FIG. 8 is a diagram for explaining a cell polarization circuit constituting polarization circuit 244. FIG. 8 is a diagram that exemplifies two adjacent ones of pMUT cells 100_1 and 100_2, and cell polarization circuits 244_1 and 244_2 corresponding to them, respectively. In actuality, polarization circuit 244 includes cell polarization circuits as many as pMUT cells 100 of pMUT element 22.

As shown in FIG. 8, cell polarization circuit 244_1 includes four switching elements S11 to S14. Similarly, cell polarization circuit 244_2 includes four switching elements S21 to S24. Each of the switching elements is, for example, a metal-oxide-semiconductor field-effect transistor (MOSFET). The gate of switching elements S11 to S14 is connected to drive circuit 243 shown in FIG. 7, and is switched on and off under the control of drive circuit 243.

As shown in FIG. 8, upper electrode 101_1 of pMUT cell 100_1 is connected to the drain of switching element S11 and the drain of switching element S12, and lower electrode 102_1 is connected to the drain of switching element S13 and the drain of switching element S14. Similarly, upper electrode 101_2 of pMUT cell 100_2 is connected to the drain of switching element S21 and the drain of switching element S22, and lower electrode 102_2 is connected to the drain of switching element S23 and the drain of switching element S24. By the above configuration, polarization control described below is performed.

[Polarization Control by Drive Circuit 243]

Drive circuit 243 performs polarization control of polarization circuit 244 based on control by ultrasound diagnostic apparatus main body 10. Hereinafter, the polarization control performed by drive circuit 243 will be described. The polarization control performed by drive circuit 243 is varied depending on connection systems of pMUT cells 100. Accordingly, a case of each of the connection systems will be described.

When the pMUT Cells are Connected in Parallel

Table 1 described below shows switching on and off control of switching elements S11 to S14 and S21 to S24 of polarization circuit 244 performed by drive circuit 243 when adjacent pMUT cells 100_1 and 100_2 are connected in parallel (FIG. 6A).

TABLE 1

| Polarization state | Cell polarization circuit 244_1 | | | | Cell polarization circuit 244_2 | | | |
|---|---|---|---|---|---|---|---|---|
| | S11 | S12 | S13 | S14 | S21 | S22 | S23 | S24 |
| PP | ON | OFF | OFF | ON | ON | OFF | OFF | ON |
| PN | ON | OFF | OFF | ON | OFF | ON | ON | OFF |
| NP | OFF | ON | ON | OFF | ON | OFF | OFF | ON |
| NN | OFF | ON | ON | OFF | OFF | ON | ON | OFF |

In Table 1, "P" and "N" in a polarization section show polarization directions of piezoelectric film 130 of pMUT cells 100_1 and 100_2 like the first embodiment, and "P" and "N" are in directions opposite to each other. Polarization direction "P" is a direction (first direction) from a lower side to an upper side, and polarization direction "N" is a direction (second direction) from the upper side to the lower side.

In Table 1, "PP" shows a state in which both pMUT cells 100_1 and 100_2 are in polarization direction "P", and "NN" shows a state in which both pMUT cells 100_1 and 100_2 are in polarization direction "N". Further, in Table 1, "PN" shows that pMUT cell 100_1 is in polarization direction "P", and pMUT cell 100_2 is in polarization direction "N", and "NP" shows that pMUT cell 100_1 is in polarization direction "N", and pMUT cell 100_2 is in polarization direction "P".

Drive circuit 243 controls switching elements S11 to S14 and S21 to S24 of polarization circuit 244 as shown in Table 1, so that transition is made between a state (non-inverted polarization) in which polarization directions of two adjacent pMUT cells 100_1 and 100_2 match with each other and a state (inverted polarization) in which the polarization directions are inverted from each other. In this manner, phase matching (at the time of inverted polarization) and phase mismatching (at the time of non-inverted polarization) of two adjacent pMUT cells 100_1 and 100_2 are achieved.

Two pMUT cells 100_1 and 100_2 connected in parallel can be deemed to be apparently connected in series at the time of inverted polarization ("PN" and "NP" in Table 1). This is because charges at upper and lower electrodes of pMUT cells 100_1 and 100_2 have opposite signs between polarization directions P and N. For example, in polarization state PN, upper electrode 101_1 with a positive charge and upper electrode 101_2 with a negative charge are connected, and lower electrode 102_1 with a negative charge and lower electrode 102_2 with a positive charge are connected.

When the pMUT cells are connected in series Table 2 described below shows switching on and off control of switching elements S11 to S14 and S21 to S24 of polarization circuit 244 performed by drive circuit 243 when adjacent pMUT cells 100_1 and 100_2 are connected in series (FIG. 6B).

TABLE 2

| Polarization state | Cell polarization circuit 244_1 | | | | Cell polarization circuit 244_2 | | | |
|---|---|---|---|---|---|---|---|---|
| | S11 | S12 | S13 | S14 | S21 | S22 | S23 | S24 |
| PP | ON | OFF | OFF | ON | OFF | ON | ON | OFF |
| PN | ON | OFF | OFF | ON | ON | OFF | OFF | ON |
| NP | OFF | ON | ON | OFF | OFF | ON | ON | OFF |
| NN | OFF | ON | ON | OFF | ON | OFF | OFF | ON |

Drive circuit 243 controls switching elements S11 to S14 and S21 to S24 of polarization circuit 244 as shown in Table 2, so that transition is made between a state (non-inverted polarization) in which polarization directions of two adjacent pMUT cells 100_1 and 100_2 match with each other and a state (inverted polarization) in which the polarization directions are inverted from each other. In this manner, like the case where the pMUT cells are connected in parallel, phase matching (at the time of inverted polarization) and phase mismatching (at the time of non-inverted polarization) of two adjacent pMUT cells 100_1 and 100_2 are achieved.

Two pMUT cells 100_1 and 100_2 connected in series can be deemed to be apparently connected in parallel at the time of inverted polarization ("PN" and "NP" in Table 2). This is because, for example, in polarization state PN, upper electrode 101_1 with a positive charge and lower electrode 102_2 with a positive charge are connected, and lower electrode 102_1 with a negative charge and upper electrode 101_2 with a negative charge are connected.

Advantageous Effect of Second Embodiment

As described above, in the second embodiment, ultrasound probe 20 includes pMUT element 22 that has an arrangement of a plurality of pMUT cells 100 including a high-frequency cell and a low-frequency cell, in which two adjacent ones of pMUT cells 100 are connected in parallel or in series, and polarization circuit 244 and drive circuit 243 that control a polarization direction of piezoelectric film 130 of pMUT cell 100. When polarization circuit 244 and drive circuit 243 control polarization directions of two adjacent pMUT cells 100_1 and 100_2 to be in opposite directions (inverted polarization), phases of two of pMUT cells 100 having different resonance frequencies are matched. In the inverted polarization state, a connection system (parallel or series) of pMUT cells 100 is apparently switched. In this manner, a characteristic of pMUT element 22 can be appropriately controlled in accordance with a purpose of use of ultrasound diagnostic apparatus 1.

Hereinafter, an advantageous effect that may be obtained by ultrasound diagnostic apparatus 1 according to the second embodiment will be described with a specific example. First, as described above, by inverted polarization of two adjacent ones of pMUT cells 100, phases of pMUT cells 100 can be matched. In this manner, like the first embodiment, lowering in sensitivity caused by phase mismatching can be prevented in pMUT element 22 as a whole.

In the second embodiment, polarization circuit 244 controls a polarization direction of pMUT cell 100, so that connection systems of adjacent ones of pMUT cells 100 can be apparently controlled.

In an ultrasound diagnostic apparatus in general, a high field intensity can be applied with a low voltage in a configuration where electrodes are disposed on both surfaces in a thick direction of a piezoelectric film having a thickness of several microns included in a pMUT cell, and a large sound pressure can be obtained. However, at the time of receiving, an obtained voltage is small as compared to stress due to a small interval between electrodes. Intensity of an ultrasound wave emitted to the inside of the body is specified for safety reasons in ultrasound diagnosis, and receiving sensitivity cannot be compensated for by transmission sound pressure. Accordingly, a predetermined receiving sensitivity needs to be ensured in order to obtain an image of high quality. As a method of compensating receiving sensitivity without increasing intensity of transmission sound pressure, there has conventionally been a method of obtaining a voltage sensitivity that is several times higher by connecting a plurality of pMUT cells in series. However, series connection generates a disadvantage that transmission sensitivity (a sound pressure value per unit voltage) is lowered.

In ultrasound diagnostic apparatus 1 according to the second embodiment, polarization directions of adjacent ones of pMUT cells 100 are inverted from each other under the control of drive circuit 243 as described above, so that a connection system (parallel or series) of pMUT cells 100 can be apparently switched. For this reason, even when pMUT cells 100 are connected in parallel, sufficient receiving sensitivity can be obtained without lowering transmission sensitivity by, for example, drive circuit 243 controlling pMUT cells 100 to have non-inverted polarization at the time of transmission and inverted polarization at the time of receiving. The above similarly applies even when pMUT cells 100 are connected in series.

Table 3 described below shows characteristics that can be obtained by polarization states and connection systems of adjacent two cells of pMUT element 22 on which pMUT cells 100 having two types of resonance frequencies coexist as described in the second embodiment.

Parallel connection in Table 3 includes apparent parallel connection, that is, pMUT cells 100, which are connected in series in actuality, are apparently connected in parallel at the time of inverted polarization. Similarly, series connection in Table 3 includes apparent series connection, that is, pMUT cells 100, which are connected in parallel in actuality, are apparently connected in series at the time of inverted polarization.

As shown in Table 3, a characteristic of pMUT element 22 can be changed depending on a combination of a polarization state and a connection system. That is, while a wide-band characteristic can be obtained by a combination in which phases are matched, a narrow-band characteristic can be obtained by intentionally mismatching phases, so that a band of high sensitivity can be used.

Effects and Advantageous Effects

The ultrasound transducer (ultrasound probe 20) of the present invention is an ultrasound transducer in which a plurality of pMUT cells (pMUT cells 100) are arranged. A plurality of the pMUT cells include a plurality of resonance frequencies. Each of a plurality of the pMUT cells includes a piezoelectric film (piezoelectric film 130) that is polarized in either the first direction that is a thickness direction and the second direction that is opposite to the first direction.

By the above configuration, the ultrasound transducer of the present invention can obtain a wide-band characteristic since phases are matched as a whole.

The ultrasound transducer of the present invention further includes a polarization circuit (polarization circuit 244) that switches a polarization direction of a piezoelectric film included in each of a plurality of pMUT cells, and a drive circuit (drive circuit 243) that controls the polarization circuit so that a plurality of pMUT cells are polarized in the first direction that is a thickness direction of a piezoelectric film of each of the pMUT cells or a second direction that is opposite to the first direction.

By the above configuration, the ultrasound transducer of the present invention can obtain not only a wide-band characteristic by matching phases of the pMUT cells, but also a variety of characteristics, such as a narrow-band characteristic by intentionally mismatching phases. Specifically, for example, when a target at a low depth needs to be imaged, priority is preferably placed on resolution by obtaining a wide-band characteristic, and when a target at a high depth needs to be imaged, priority is preferably placed on sensitivity by obtaining a narrow-band characteristic. Alternatively, for example, a signal loss may be restricted by increasing capacitance (lowering impedance) of pMUT element 22 at the time of transmission, and receiving sensitivity may be obtained by lowering capacitance (increasing impedance) at the time of receiving.

TABLE 3

| Polarization state | Connection system | |
|---|---|---|
| | Parallel connection | Series connection |
| Non-inverted polarization (PP, NN) | Narrow band (high sensitivity) High capacity (low impedance) | Wide band (high resolution) Low capacity (high impedance) |
| Inverted polarization (PN, NP) | Wide band (high resolution) Low capacity (high impedance) | Narrow band (high sensitivity) High capacity (low impedance) |

Modifications

In the above embodiment, pMUT element 22 may be a 2D array on which pMUT cells 100 are arranged two-dimensionally as shown in FIG. 5, as well as a 1D array, a 1.5D array, or the like on which pMUT cells 100 are arranged one-dimensionally.

In the above embodiment, pMUT element 22 has the configuration in which high-frequency cells 110 and low-frequency cells 120 are arranged alternately in vertical and horizontal directions as shown in FIG. 5. However, the present invention is not limited to this configuration. In the present invention, for example, high-frequency cells 110 and low-frequency cells 120 may be arranged alternately only in a vertical direction or a horizontal direction. High-frequency cells 110 and low-frequency cells 120 do not need to be at an equal ratio, and may be arranged unequally. When high-frequency cells 110 and low-frequency cells 120 are not at an equal ratio, a characteristic of entire pMUT element 22 varies depending on which of high-frequency cells 110 and low-frequency cells 120 are larger in number. Accordingly, the ratio may be changed depending on a purpose.

In the above embodiment, pMUT element 22 has arrangement of pMUT cells 100 having two types of resonance frequencies. However, the present invention is not limited to the above configuration. In the present invention, the pMUT element may be configured with arrangement of pMUT cells having, for example, three types or more of resonance frequencies. When pMUT cells having three types of more of of resonance frequencies are arranged, the pMUT cells may be arranged equally or unequally between each resonance frequencies, like the above configuration. The ratio of pMUT cells between each resonance frequency may be changed as appropriate in a designing stage of ultrasound diagnostic apparatus 1.

In the above embodiment, the method of differentiating the diameter of piezoelectric film 130 is employed as a method of modulating a frequency of high-frequency cell 110 and low-frequency cell 120. However, the present invention is not limited to the method. In the present invention, high-frequency cell 110 and low-frequency cell 120 may have different resonance frequencies by, for example, differentiating the thickness of piezoelectric film 130 or by filling an opening section provided on a substrate that supports piezoelectric film 130 with different materials.

INDUSTRIAL APPLICABILITY

The present invention can be used for an ultrasound transducer that transmits and receives an ultrasound wave by using a pMUT.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasound transducer comprising:
a plurality of piezoelectric micromachined ultrasound transducer (pMUT) cells that are arranged in an array, wherein:
the plurality of pMUT cells each have one of a plurality of resonance frequencies,
each of the plurality of pMUT cells includes a piezoelectric film that is polarized in a first direction that is a thickness direction or a second direction that is opposite to the first direction,
piezoelectric films of different pMUT cells among the plurality of pMUT cells have different polarization directions when the different pMUT cells have different resonance frequencies, and
the piezoelectric film of each of the plurality of pMUT cells is polarized in the first direction or the second direction before a drive signal for causing the transducer to transmit an ultrasound wave is applied to the plurality of pMUT cells, such that, at a time of applying the drive signal to the plurality of pMUT cells, the piezoelectric film of each of the plurality of pMUT cells is already polarized in the first direction or the second direction.

2. The ultrasound transducer according to claim 1, wherein:
the plurality of pMUT cells have two types of resonance frequencies that are different from each other.

3. The ultrasound transducer according to claim 1, further comprising:
a polarizer configured to switch a polarization direction of the piezoelectric film of each of the plurality of pMUT cells to the first direction or the second direction; and
a controller configured to control the polarizer to switch the polarization direction of the piezoelectric film to the first direction or the second direction.

4. The ultrasound transducer according to claim 3, wherein:
the controller controls the polarizer so that two adjacent ones of the plurality of pMUT cells are polarized in directions different from each other.

5. The ultrasound transducer according to claim 3, wherein:
the controller controls the polarizer so as to switch a piezoelectric direction of each of the plurality of pMUT cells based on a target part to be imaged by the ultrasound transducer.

6. The ultrasound transducer according to claim 3, wherein:
the controller controls the polarizer so as to switch the piezoelectric direction of each of the plurality of pMUT cells between a time of transmitting and a time of receiving an ultrasound wave using the ultrasound transducer.

7. An ultrasound diagnostic apparatus comprising the ultrasound transducer according to claim 1.

8. The ultrasound transducer according to claim 3, wherein:
the controller controls the polarizer such that two adjacent ones of the plurality of pMUT cells are polarized in a same direction at a time of transmitting an ultrasound wave and are polarized in directions inverted with respect to each other at a time of receiving an ultrasound wave.

* * * * *